United States Patent
Parsai et al.

(10) Patent No.: US 9,480,859 B2
(45) Date of Patent: *Nov. 1, 2016

(54) UNFILTERED RADIATION THERAPY

(71) Applicant: The University of Toledo, Toledo, OH (US)

(72) Inventors: E. Ismael Parsai, Toledo, OH (US); John J. Feildmeier, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,275

(22) Filed: Apr. 20, 2016

(65) Prior Publication Data

US 2016/0236010 A1  Aug. 18, 2016

Related U.S. Application Data

(62) Division of application No. 12/224,015, filed as application No. PCT/US2007/004403 on Feb. 20, 2007, now Pat. No. 9,370,672.

(60) Provisional application No. 60/775,677, filed on Feb. 21, 2006.

(51) Int. Cl.
*A61N 5/10* (2006.01)
*G21K 1/04* (2006.01)
*G21K 5/00* (2006.01)

(52) U.S. Cl.
CPC ........... *A61N 5/1042* (2013.01); *A61N 5/1045* (2013.01); *A61N 5/1077* (2013.01); *G21K 1/046* (2013.01); *G21K 5/00* (2013.01); *A61N 2005/1034* (2013.01)

(58) Field of Classification Search
CPC .. A61N 5/103; A61N 5/1042; A61N 5/1045; A61N 5/1047; A61N 2005/1034
See application file for complete search history.

(56) References Cited

U.S. PATENT DOCUMENTS

| | | | | | |
|---|---|---|---|---|---|
| 4,868,843 | A | * | 9/1989 | Nunan | G21K 1/046 250/505.1 |
| 5,216,255 | A | * | 6/1993 | Weidlich | G21K 1/04 250/492.3 |
| 5,332,908 | A | * | 7/1994 | Weidlich | A61N 5/1042 250/492.1 |
| 5,596,619 | A | * | 1/1997 | Carol | A61N 5/01 378/150 |
| 5,668,371 | A | * | 9/1997 | Deasy | A61N 5/1042 250/505.1 |
| 5,802,136 | A | * | 9/1998 | Carol | A61N 5/01 378/150 |
| 6,038,283 | A | * | 3/2000 | Carol | A61N 5/1031 378/65 |
| 6,393,096 | B1 | * | 5/2002 | Carol | A61N 5/1031 378/151 |
| 7,162,008 | B2 | * | 1/2007 | Earl | A61N 5/1031 378/149 |
| 7,295,649 | B2 | * | 11/2007 | Johnsen | A61N 5/103 378/65 |
| 7,400,434 | B2 | * | 7/2008 | Brahme | G21K 1/046 359/237 |
| 7,907,697 | B2 | * | 3/2011 | Maltz | G06T 11/005 378/7 |
| 7,945,022 | B2 | * | 5/2011 | Nelms | A61N 5/1071 378/65 |
| 7,961,843 | B2 | * | 6/2011 | Brown | A61N 5/103 378/65 |

(Continued)

*Primary Examiner* — Thomas R Artman
(74) *Attorney, Agent, or Firm* — Emch, Schaffer, Schaub & Porcello Co., L.P.A.

(57) ABSTRACT

This is a new technique of producing high energy X-rays for radiation therapy at a patient's level. The dose delivery system uses a linear accelerator with no flattening filter. The technique improves patient radiation therapy by reducing radiation scattered to surrounding normal tissue and reducing electron contamination. It increases dose rate to shorten treatment time. The flattening filter reduces the efficiency of the beam by reducing the fluence and increasing scattered radiation. This technique involves removal of the flattening filter. It uses inverse planning to shape the dose distribution.

11 Claims, 8 Drawing Sheets

(56) References Cited

U.S. PATENT DOCUMENTS

| | | | | |
|---|---|---|---|---|
| 8,027,431 B2* | 9/2011 | Stahl | A61N 5/103 378/65 |
| 8,050,384 B2* | 11/2011 | Carol | A61N 5/10 378/64 |
| 2004/0071261 A1* | 4/2004 | Earl | A61N 5/1031 378/65 |
| 2004/0082855 A1* | 4/2004 | Robar | A61N 5/10 600/436 |
| 2007/0086569 A1* | 4/2007 | Johnsen | A61N 5/103 378/65 |
| 2008/0049897 A1* | 2/2008 | Molloy | A61N 5/1042 378/65 |
| 2008/0118032 A1* | 5/2008 | Graham | G21K 1/046 378/152 |
| 2008/0170663 A1* | 7/2008 | Urano | A61N 5/1042 378/65 |
| 2008/0191141 A1* | 8/2008 | Nilsson | A61N 5/1048 250/393 |
| 2010/0305905 A1* | 12/2010 | Ehringfeld | A61N 5/1048 702/189 |
| 2011/0033028 A1* | 2/2011 | Parsai | A61N 5/1042 378/65 |

* cited by examiner

UNFILTERED RADIATION THERAPY

CROSS REFERENCE TO RELATED APPLICATIONS

This divisional application claims the benefit of U.S. provisional patent application: Ser. No. 60/775,677, filed Feb. 21, 2006; PCT application serial no. PCT/US2007/04403, filed Feb. 20, 2007; and U.S. utility patent application Ser. No. 12/224,015, filed Oct. 13, 2010.

TECHNICAL FIELD

This invention relates to a method of performing radiation therapy. More specifically the invention relates to a new technique in IMRT conformal gamma radiation dose delivery using a linear accelerator with no flattening filter. The new technique improves patient radiation therapy by reducing radiation scattered to surrounding normal tissue without a filter.

BACKGROUND OF THE INVENTION

Intensity modulated radiation therapy (IMRT) is a treatment method for cancer patients requiring radiation treatment. IMRT is an extremely precise method of treatment delivery where the radiation dose conforms to the target and avoids the surrounding critical structures. Rather than having a single large radiation beam pass through the body, with IMRT the treatment is delivered from various angles and the intensity of the radiation beam is varied across the treatment area.

The radiation is effectively broken up into thousands of tiny pencil-thin radiation beams. With millimeter accuracy, these beams enter the body from many angles and intersect on the cancer. This results in a high radiation dosage to the tumor and a lower radiation dose to the surrounding healthy tissues.

One method for modulating the intensity of the radiation beam is based upon moving a multi-leaf collimator (MLC) in and out of radiation beam from the radiation treatment machine. An MLC comprises a plurality of thin width mechanical blades or leaves, which are individually controlled by miniature motors and mechanical drive linkages. A computer controls the miniature motors for driving the individual blades in and out to shape the radiation beam. An advantage of an MLC based IMRT treatment machine is that the same MLC can be automatically controlled to support the individual needs of each patient receiving radiation treatment. In other words, the MLC is reconfigured for each new patient.

Linear accelerators have for decades come with a photon flattening filter to make the photon profile of planar fluence and thus, the dose distribution more uniform. These filters have then resulted in fluence attenuation and contamination of the beam. Now in the age of techniques such as intensity modulated radiation therapy (IMRT) the function of the flattening filter becomes redundant and the flattening filter now merely reduce the efficiency of the beam by reducing the fluence and increase scattered radiation.

Other objects and advantages of the present invention will become apparent to those skilled in the art upon a review of the following detailed description of the preferred embodiments and the accompany drawings.

SUMMARY OF THE INVENTION

Our technique involves removal of the flattening filter for complex treatments and using inverse planning along with multi-leaf collimators to shape the dose distribution.

With the flattening filter removed the dose rate is increased and he lateral scatter is reduced. This improves patient treatment by reducing dose to the normal tissue surrounding the target and also reduces treatment times. The flattening of the beam profile is redundant in techniques such as IMRT since the planar fluence is controlled by the multi-leaf collimator (MLC). For many modern linear accelerators, removal of the flattening filter requires no physical modification of the unit since the flattening filter can simply be mechanically moved out of the beam path.

This new technique is in IMRT and 3D conformal gamma radiation dose deliver using a linear accelerator with no flattening filter. The technique improves patient radiation therapy by reducing radiation scattered to surrounding normal tissue and reducing electron contamination. It increases does rate to shorten treatment time.

Linear accelerators have for decades come with a photon flattening filter to make the photon profile of planar fluence to make the dose distribution more uniform. These filters, however, have resulted in fluence attenuation and contamination of the beam.

Now in the age of techniques such as intensity modulated radiation therapy (IMRT) the function of the flattening filter becomes redundant. The flattening filter now merely reduces the efficiency of the beam by reducing the fluence and increasing scattered radiation.

DETAILED DESCRIPTION OF THE INVENTION

Figure 1A:
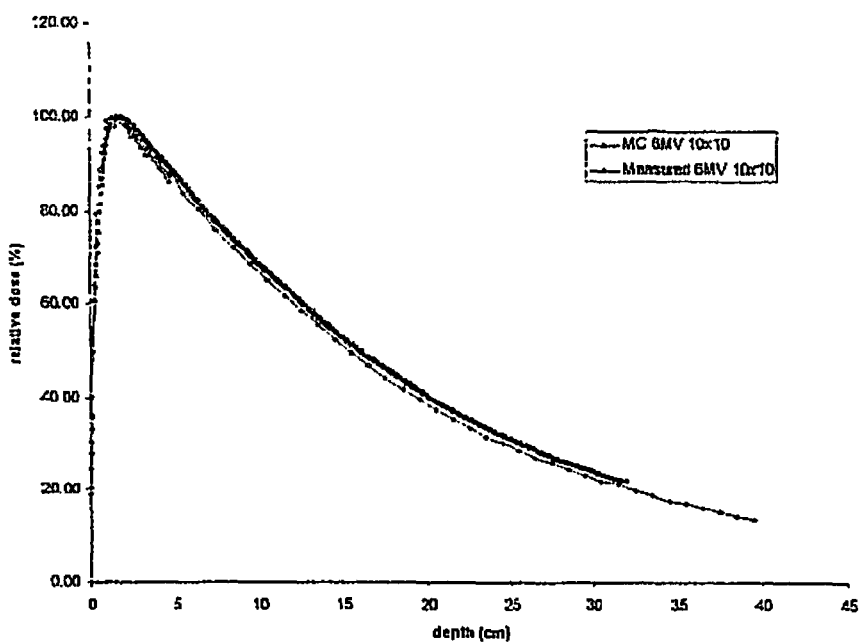
FIGS. 1(*a*) and 1(*b*) show Monte Carlo and water phantom measurements of the CAX percent depth-dose for 6 MV and 10 MV.

IMRT (Intensity Modulated Radiation Therapy) is rapidly becoming a common treatment modality with a recent study claiming that it is used by a third of the radiation oncologists in the United States. The modern treatment machines are designed with dynamic MLC and IMRT-ready systems integrated into them but many of the current linear accelerators still used today, have the MLC as an add-on. In either case the linear accelerator is designed such that IMRT treatments and standard treatments can be carried out on the same unit. The conventional 3D conformal therapy treatment requires a flat beam because generally dose compensation to achieve uniformity within target volume for each individual beam is not performed. However, in generating IMRT treatment plans, the planner ends up with a non-uniform density matrix to deliver the desired dose with the target volume, and spare the surrounding normal or critical structures. To achieve this goal, a flat beam is not required. Modulation of beam during IMRT planning and delivery is performed through segmented fields and many beamlets within the delivery port and in fact thinking out side of convention, one would see the advantages in having a cleaner beam that does not need to suffer all the scattering through a thick chunk of metal, namely the flattening filter. It is therefore, expected that removal of the flattening filter would lead to better IMRT treatments due to the reduction in lateral photon scatter and the increase in central axis photon fluences. More specifically, by moving the flattening filter out of the path of the beam solely for IMRT treatments, higher dose rates and sharper, more geometrically defined fields can be expected thus leading to better IMRT plans and treatments. The deleterious properties of the flattening filter care caused by the increased lateral scatter and the decreased central axis fluence that the filter produces. In the special case of IMRT, where fluence is varied by a combination of MLC movements and beam modulation at the patient level, the filter is no longer required. This has been shown for the specific case of tomotherapy; a dedicated IMRT system. Here we show Monte Carlo simulations of radiation characteristics for the more general case of a linear accelerator. Preferably, the higher dose rates are X-rays ranging from 4 MV to 25 MV.

Methods and Materials
Monte Carlo Simulations of an Elektra SL-25

Monte Carlo simulations were carried out using the BEAMnrc code. Using an Elektra precise model SL-25 photon beams of 6 MV and 10 MV energies were initially modeled and commissioned by comparing the simulations to data measured using a Welhofer (Scanditronix Wellhofer) scanning water phantom. In the models the head of the accelerator was broken down into component modules, namely the target, primary collimator, flattening filter, monitor chamber, mirror, MLC and X and Y jaws. An additional component was used to simulate the air gap between the exit of the accelerator and the water phantom surface, where the phase space plane was located. The energy cutoffs for transport were set as ECUT=0.7 MeV, PCUT-0.01 MeV and global electron cut-off-2.0 MeV. Electron range rejection and selective Bremsstahlung splitting were used, with SBS parameters $N_{min}$=10 nd $N_{max}$=100. Russian roulette and photon forcing were not employed. The phase space file created at the plane 100 cm from the source was then used as the input for the phantom, simulated using the DOSXYZ-arc code. $400 \times 10^6$ histories were used for the simulation of the accelerator. For the DOSXYZ phantom, $200 \times 10^6$ histories were used for all field sizes, resulting in adequate statistics for the larger field sizes.

Both depth dose and transverse profiles depend greatly on the properties of the electron beam as it strikes the photon target. The parameters of importance are the mean electron energy, the energy spread and the spatial distribution of the beam. For the 6 MV and 10 MV beams respectively, the electron energy used was 6.50 MeV and 9.50 MeV, the energy spread was 1.0 MeV and 0.8 MeV FWHM and the radial distribution was 0.11 cm and 0.10 cm FWHM. Depth dose curves obtained from these simulations deviated less than 1% in the region of dose-maximum and less than 5% at all other depths, when compared to water phantom measurements.

Once the Monte Carlo simulation was found to match the measured data to adequate levels, the flattening filters were removed from both of the 6 MV and 10 MV beam models. All other parameters remained unchanged.

Measurements Made in Water.

All measurements were made at 100 cm SSD in a Welhofer scanning water phantom, with a 0.1 cc ionization chamber. Both 6 MV and 10 MV beams were studied for comparison with the Monte Carlo simulations. After the Monte Carlo model commissioning data was obtained the 6 MV and 10 MV flattening filters were removed from the primary rotating carousel in the head of the accelerator. This left a hole in the carousel which the photon beam could pass through. Depth-ionization profiles, transverse inline (gun-target direction) and cross-plane profiles were measured at $d_{max}$ and 10 cm. Depth dose profiles were measured to a depth of 30 cm and normalized to the maximum chamber reading on the central axis. Transverse profiles were measured in the inline and cross-plane directions for field sizes ranging from 5×5 to 30×30 $cm^2$. These profiles were also normalized to the maximum chamber reading on the central axis.

Results
Monte Carlo Model Commissioning

As mentioned, Monte Carlo simulations of the standard, flattened 6 MV and 10 MV beams where carried and they matched well with the measured data obtained with the scanning water phantom. The purpose of these measurements was to show that the Monte Carlo models accurately match the measurements of dose performed in the water phantom.

Figure 1B:
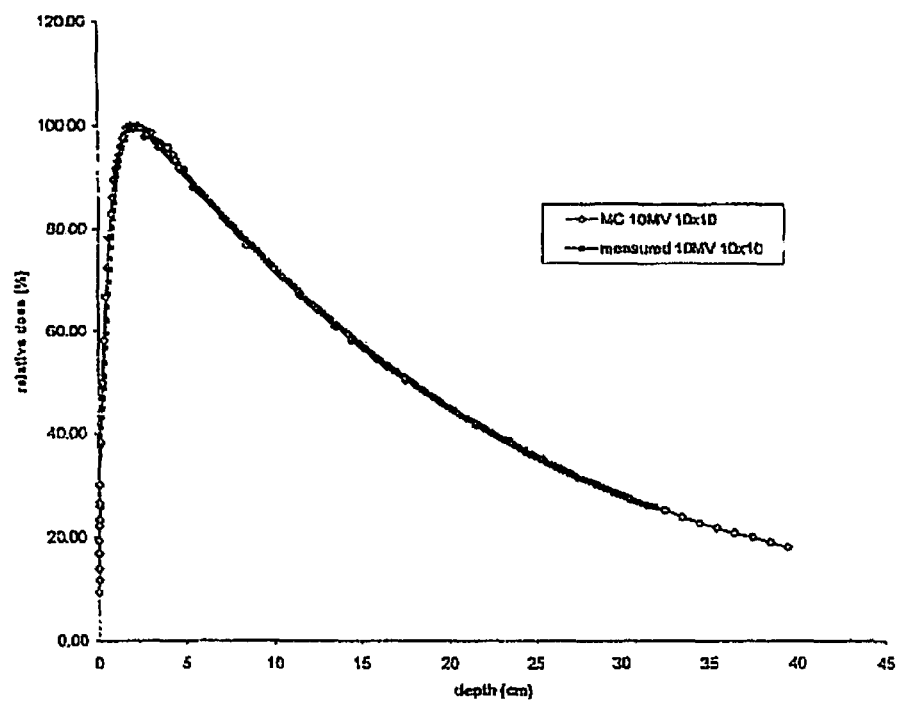

FIGS. 1(a) and 1(b) show Monte Carlo and water phantom measurements of the CAX percent depth-dose for 6 MV and 10 MV. Central axis percent depth-dose profiles for a 10×10 $cm^2$ field at 100 cm SSD are shown for 6 MV and 10 MV, with the experimental measurements shown as solid points and the Monte Carlo model shown as hollow points. Transverse profiles of a 30×30 $cm^2$ field were also obtained for comparison of the flatness and symmetry of the Monte Carlo models with respect to the measured data.

Figure 2A:
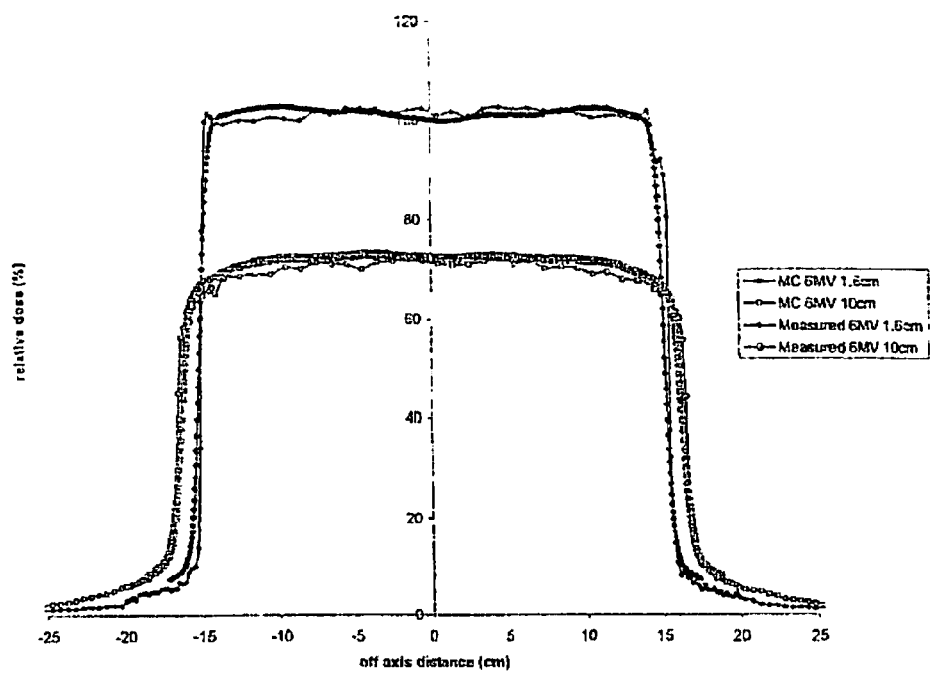
FIGS. 2(*a*) and 2(*b*) show Monte Carlo and water phantom measurements of transverse profiles at depths $d_{max}$ and 10 cm, for 6 MV and 10 MV.
Figure 2B:
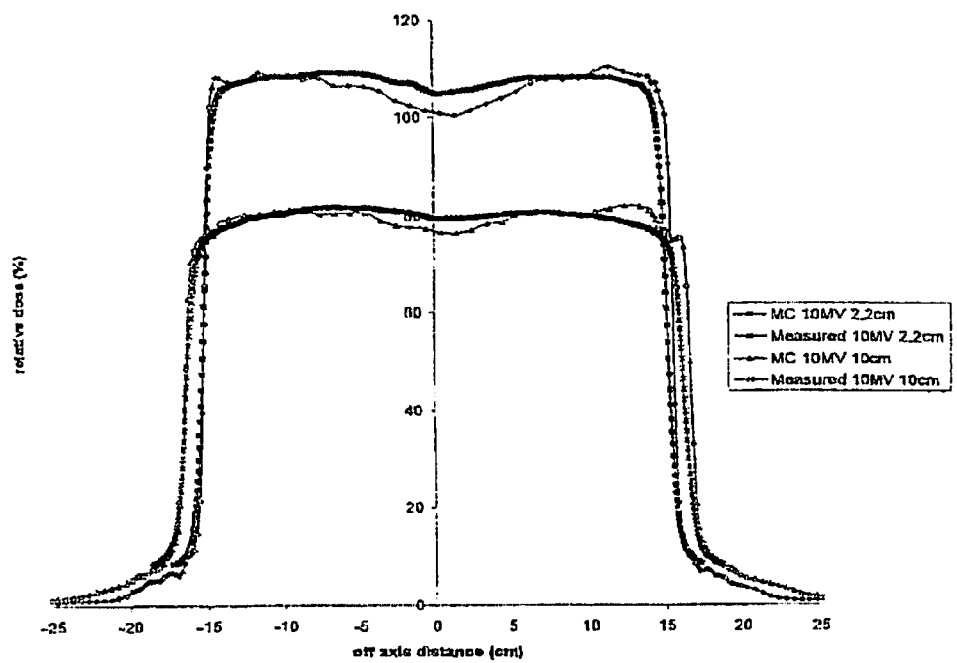

FIGS. 2(a) and 2(b) show 6 MV and 10 MV Monte Carlo calculated transverse profiles for the inline direction at depths of $d_{max}$ and 10 cm, compared to the measured data. A good agreement between measured and Monte Carlo modeled data was found in all cases.

Figure 3:
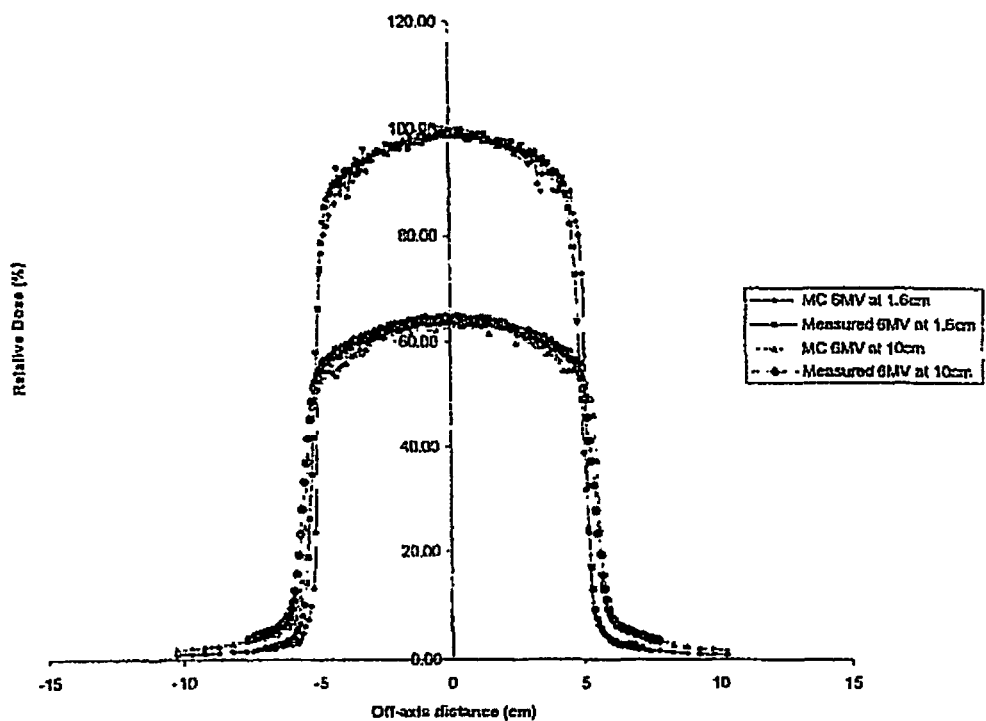
FIG. 3 shows a comparison between Monte Carlo and measured data for a 6 MV 10×10 cm² beam.

FIG. 3 shows a comparison between Monte Carlo and measured data for a 6 MV 10×10 cm2 beam. The top two curves are for a depth of 1.6 cm ($d_{max}$) and the bottom two curves are for a depth of 10 cm.

Monte Carlo Modelling of a Non-Flat Beam

Simulations were then carried out without the filter and compared to data measured after the flattening filters had been removed from the primary filter carousel of the Elekta accelerator. The purpose of these measurements was to verify the accuracy of the Monte Carlo models to accurately simulate a beam without the flattening filter. A comparison for the cross-plane profiles is shown in FIG. 3.

Not shown are the comparisons between the inline (gun-target) direction measured and Monte Carlo profiles. These measured transverse profiles had poor symmetry and this was believed to be due to difficulties of steering the beam after removal of the flattening filter. It can be concluded from FIG. 3 that the Monte Carlo models of filter free 6 MV and 10 MV beams were shown to accurately match the measured data. Simulations were then carried out for various field sizes ranging from 2×2 cm² to 30×30 cm². The graph below shows the transverse profiles obtained at 1.6 cm depth for a 6 MV beam without a flattening filter. The curves in FIG. 4 are all normalized to the CAX dose of the 10×10 cm² field.

Figure 4:
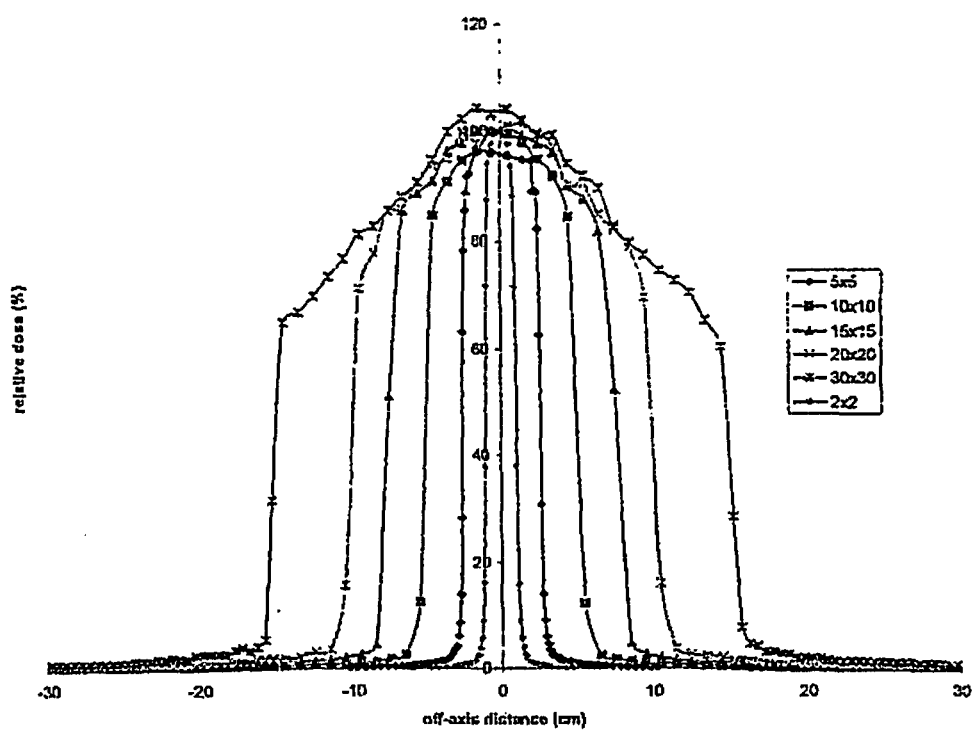
FIG. 4 shows a Monte Carlo computed transverse cross-plane profiles at a depth of 1.6 cm for a 6 MV filter free photon beam of field size ranging from 2×2 to 30×30 cm².

FIG. 4 shows Monte Carlo computed transverse cross-plane profiles at a depth of 1.6 cm for a 6 MV filter free photon beam of field size ranging from 2×2 to 30×30 cm².

The next step was to compare the Monte Carlo models of the flattened and unflattened beams. FIG. 5 shows Monte Carlo calculated transverse profiles and the effect on the central axis (CAX) dose of removing the flattening filter. It was found that for the 6 MV photon beam of 10×10 cm² field size the CAX dose was increased by a factor of 2.35 with the filter removed, compared to the standard flattened beam. This figure also shows the CAX dose was increased by a factor of 2.35 with the filter removed, compared to the standard flattened beam. This figure also shows the CAX dose for a 10×10 cm² 10 MV beam with and without the flattening filter. In this case, since the 10 MV flattening filter for the Elekta is more substantial in terms of mass of material used the CAX dose without the filter is 4.18 times higher than the standard flattened beam.

Figure 5A:
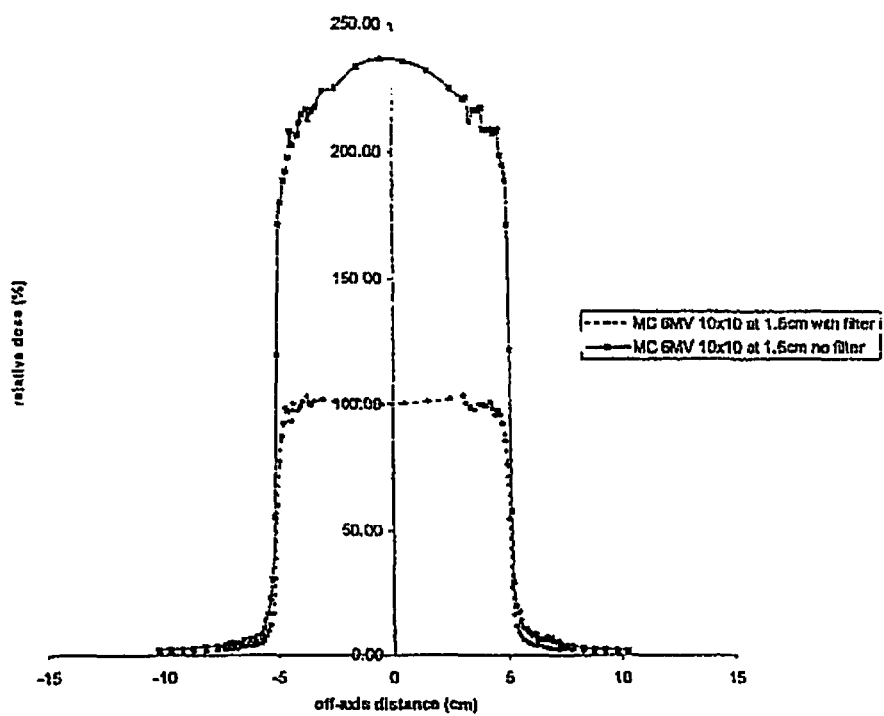
FIGS. 5(*a*) and 5(*b*) shows a comparison between Monte Carlo simulations for a standard, flattened and an unflattened 6 MV and 10 MV 10×10 cm² beam at $d_{max}$. All profiles are normalized to the central axis does of the standard beam to show the effect on the CAX dose of removing the flattening filter.
Figure 5B:
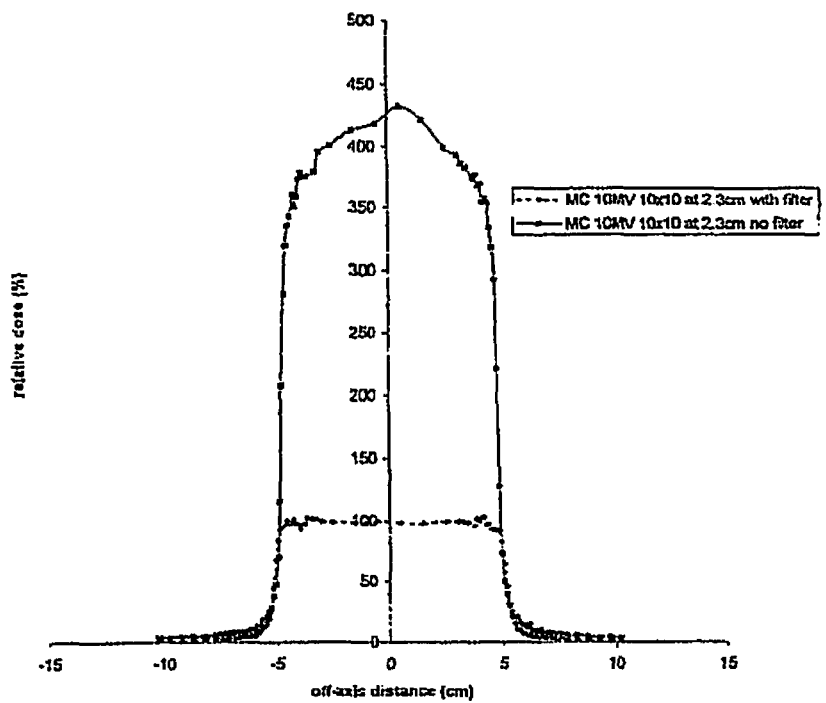

FIGS. 5(a) and 5(b) show a comparison between Monte Carlo simulations for a standard, flattened and an unflattened 6 MV and 10 MV 10×10 cm² beam at $d_{max}$. All profiles are normalized to the central axis dose of the standard beam to show the effect on the CAX dose of removing the flattening filter.

C. Quantification of Beam Flatness

The flatness of each transverse profile was calculated using the variation over the mean at 80% of the field size, with the equation, $$\text{flatness} = 100 \times \frac{D_{max} - D_{min}}{D_{max} + D_{min}}$$

For the 6 MV simulation of a 10×10 cm² beam, the flatness at $d_{max}$ was 2.37% and 6.21% for the flattened ad unflattened beam, respectively. Similarly, at 10 cm depth the equivalent percentages were 1.88% and 5.77%.

For the 10 MV simulations, flatness percentages of 3.96% and 7.71% were obtained at depths of 2.3 cm ($d_{max}$) and 10 cm for the standard and unflattened beam, respectively. At 10 cm depth flatness was calculated to be 2.92% for the flattened beam and 8.39% for the unflattened beam.

D. Dose on the Central Axis

Figure 6A:
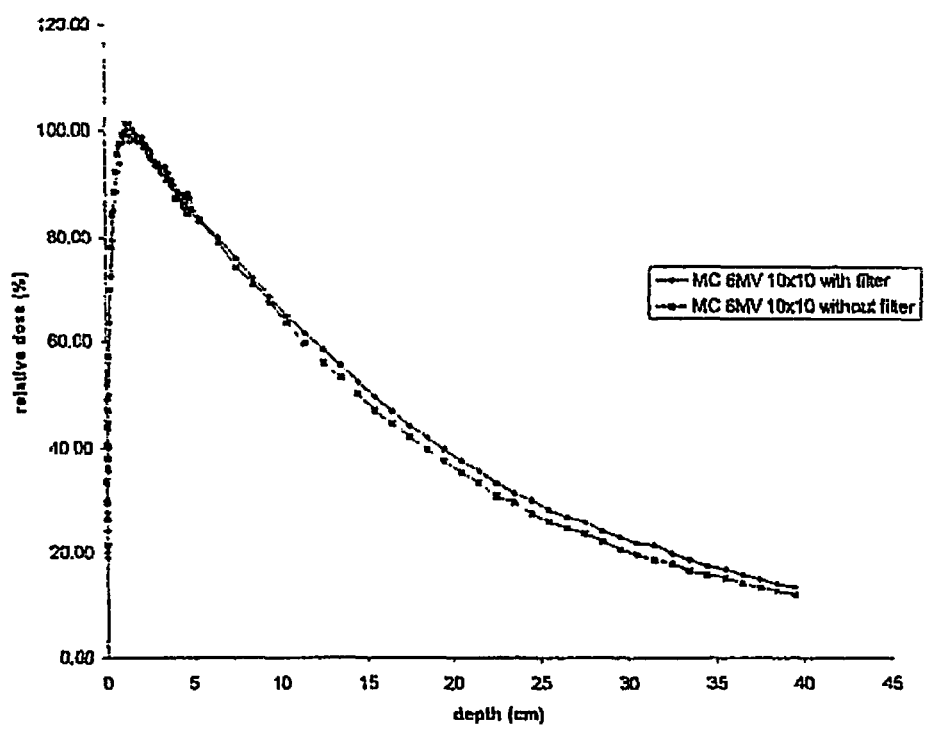
FIGS. 6(*a*) and 6(*b*) shows a Monte Carlo percent depth-dose curves comparing the standard flattened 6 MV and 10 MV beams to the equivalent filter-free beams.
Figure 6B:
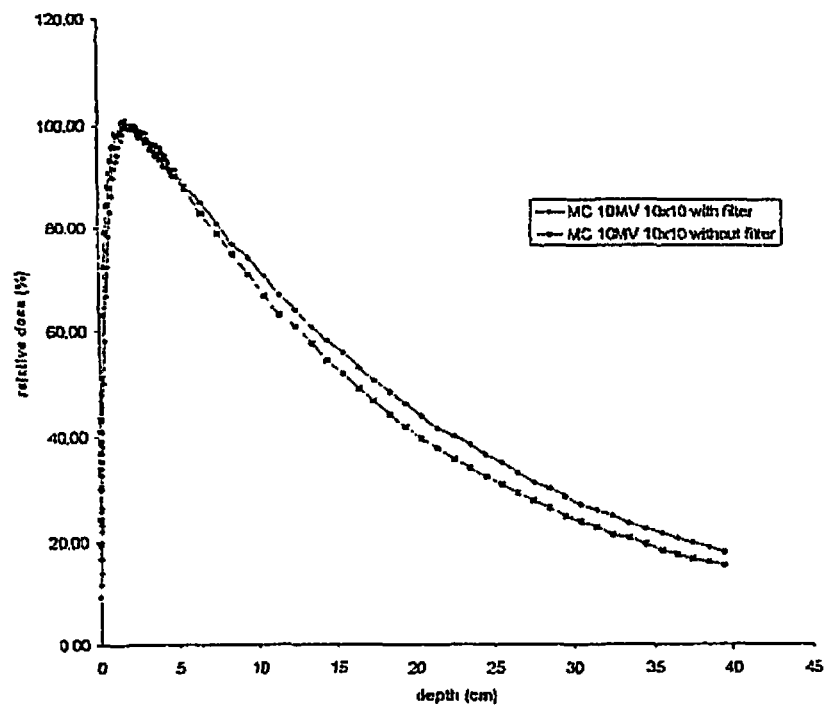

FIGS. 6(a) and 6(b) show Monte Carlo percent depth-dose curves comparing the standard flattened 6 MV and 10 MV beams to the equivalent filter-free beams. The faster decrease in dose with depth for the filter-free beam is consistent with a softer central axis beam.

Depth dose curves on the central axis were also obtained from simulations of the flattened and unflattened 10×10 cm2 6 MV and 10 MV beams. The dose deposited at depths greater than $d_{max}$ was found to decrease more rapidly with the filter removed. This is due to the fact that, with the filter removed the beam in the region of the central axis is no longer hardened by the filter. The faster decrease in dose with depth is consistent with a softer central axis beam. To investigate the effect of the flattening filter on the photon energy spectrum an analysis of various phase space files with the program BEAMDP was performed. Photon fluence as a function of photon energy was graphed for the filter free beams versus the standard Beams. As expected, the photon fluence per unit energy is significantly greater for the filter free beam, especially in the region of the peak photon energy.

Figure 7A:
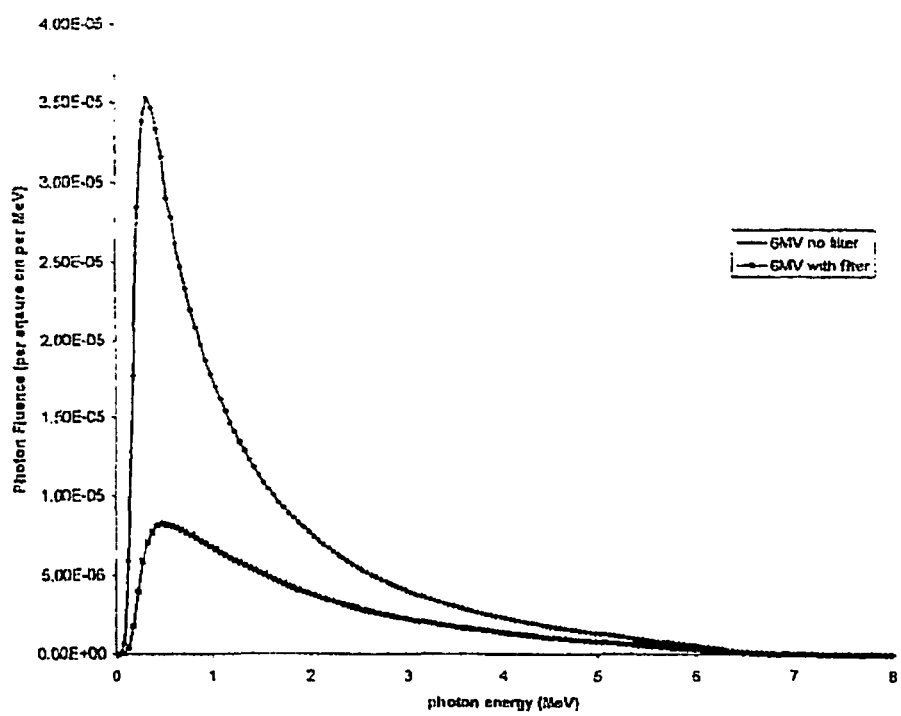
FIGS. 7(*a*) and 7(*b*) show a photon fluence spectra for a 6 MV beam and a 10 MV beam showing the effect of removing the photon flattening filter.
Figure 7B:
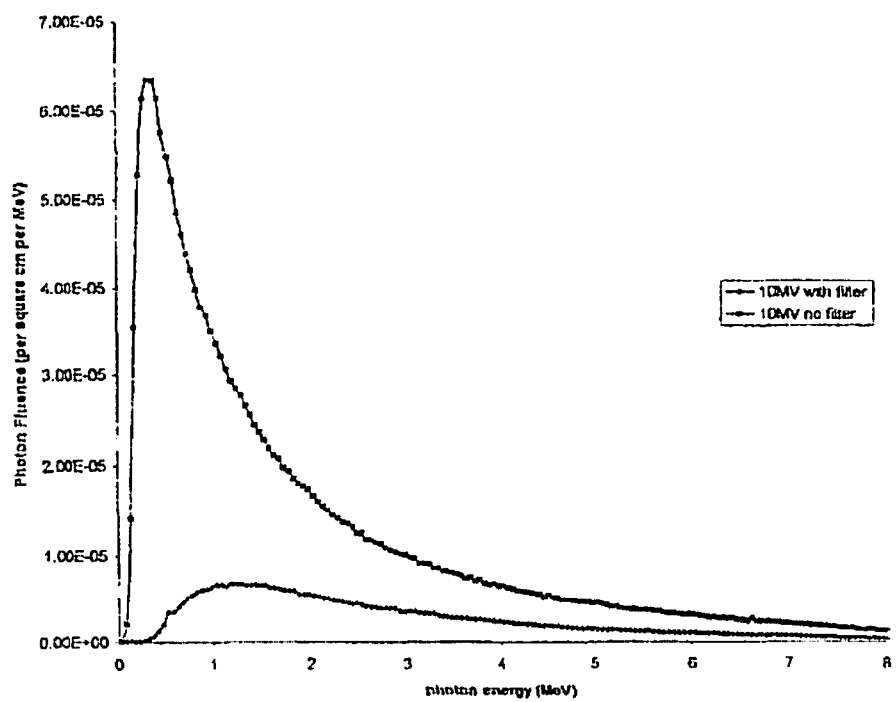

FIGS. 7(a) and 7(b) show photon fluences spectra for a 6 MV beam and a 10 MV beam showing the effect of removing the photon flattening filter. FIG. 7 shows the photon fluence spectra across a 10×10 cm² field for both the 6 MV and the 10 MV beam. In both cases the peak photon energy is increased by removing the flattening filter, showing that the flattening filter has the effect of hardening the beam. For the 6 MV beam the peak energy with and without the flattening filter are 0.48 MV and 0.33 MeV respectively. Similarly, for the case of the 10 MV beam, where the design of the flattening filter leads to a greater beam hardening effect, the peak photo energies are 1.13 MeV and 0.33 MeV for the standard beam and the filter free beam.

E. Out of Field Dose

Figure 8:
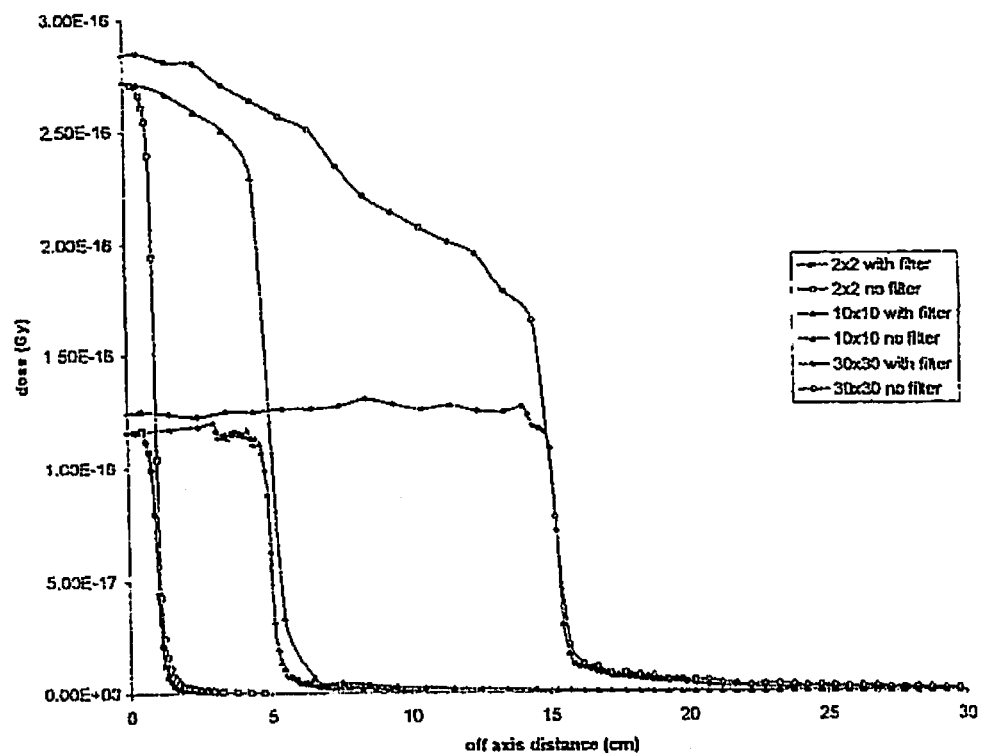
FIG. 8 shows a comparison of absolute does obtained from simulations of 2×2, 10×10 and 30×30 cm² fields. The simulations shown here were for a 6 MV beam at a depth of 1.6 cm.

With the flattening filter removed, one would expect the amount of lateral photon scatter to decrease, the effect being that the dose at a point outside the field would be reduced. To investigate this effect a comparison between the relative dose at and beyond the edge of the radiation field was made between simulations made of a 6 MV beam with and without the flattening filter. Simulations were run for a 6 MV beam for various field sizes ranging from 2×2 cm² to 30×30 cm². In all cases the dose at the edge of the field was greater for the filter-free beam. In FIG. 8 below, 2×2 cm², 10×10 cm² and 30×30 cm² fields are shown for a flattened and filter-free 6 MV beam. It can be seen that, in the wings of the profile the relative dose for the filter-free beam is greater than that of the standard field in all cases. The profiles below are at a depth of 1.6 cm. The same profiles at a depth of 10 cm showed the same effect; the out of field dose being higher for the filter free beam.

FIG. 8 is a comparison of absolute dose obtained from simulations of 2×2, 10×10 and 30×30 cm² fields. The simulations shown here were for a 6 MV beam at a depth of 1.6 cm. For each field size a profile of the flattened beam and the unflattened beam are shown so that the dose at the edges of the radiation field can be compared. It can be seen that for all field sizes the dose at the edge of the field is greater for the filter-free beam.

To quantify the out of field dose were considered a point 2 cm outside of the field (e.g. at an off axis distance of 3 cm for a 2×2 cm² field) and took the average of the relative doses for the voxels to the right and left of the central axis. The table below shows the relative dose (the normalization is with respect to the CAX dose for the standard, flattened beam for that field size) at a point 2 cm outside the radiation field, for both the flattened and unflattened 6 MV beams. All profiles considered here are at a depth of maximum dose.

TABLE 1

|  | Relative Dose (0%) | |
| --- | --- | --- |
|  | with filter | No filter |
| 2 × 2 cm² | 0.63 | 1.10 |
| 10 × 10 cm² | 2.86 | 4.55 |
| 30 × 30 cm² | 6.03 | 7.64 |

Table 1. Shows a comparison of out of field relative dose for various field sizes. For each field size the relative doses is given at a point outside or on the edge of the radiation field.

CONCLUSIONS

With flattening filter removed, the photon beams will not suffer the remarkable scattering that they will go through otherwise, resulting in a much cleaner beam at the patient's level. The conventional treatments requiring a flat photon beam are not necessary for IMRT treatments as the beams are modulated to achieve dose uniformity within the target volume. In fact the fluence maps as generated from a beam end up being very nonuniform for IMRT cases. The substantial increase in dose rate from a flattening filter free accelerator is significant in delivering a less contaminated beam at much shorter times. The computed depth dose plots for both 6 and 10 MV photon beams indicate that by removing the flattening filter out of the beam, better dose fall off beyond depth of maximum dose is achieved. On the other hand, because of a less hardened beam, the point of maximum dose ate depth will get closer to the surface (1-2 mm for 6×, and 2-3 mm for 10×). The out of field dose is a phenomenon that requires further study and will be discussed in detail in future works, but the measured and computed dose profiles in treatment fields indicate less scatter, significantly higher photon fluence, and overall a cleaner beam to be used for the IMRT treatment. The better fall-off of the dose beyond depth of maximum dose in a flattening free accelerator is also another indication to cleaner beams when filter is removed. The quantities of scatter and lower energy photons contributing to dose depth is directly proportional to the energy of the beam and is considerable for clinical photon beams.

Modifications

Specific compositions, methods, or embodiments discussed are intended to be only illustrative of the invention disclosed by this specification. Variation on these compositions, methods or embodiments are readily apparent to a person of skill in the art based upon the teachings of this specification and are therefore intended to be included as part of the inventions disclosed herein.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. A method for producing high energy X-rays for radiation therapy at patient's level comprising the steps of:
   using a linear accelerator without a flattening filter to provide a high radiation dose having a dose distribution;
   wherein the radiation dose is high energy X-rays ranging from 6 MV to 25 MV;
   using inverse planning to shape the dose distribution, increase dose rate and shorten treatment time; and
   radiating a patient in need of radiation therapy with the shaped radiation field.

2. A method according to claim 1 including the step of improving patient radiation therapy by reducing radiation scattered to surrounding normal tissue and reducing electron contamination.

3. A method according to claim 1 including the step of delivering a less contaminated radiation beam at shorter treatment times.

4. A method according to claim 1 including the step of delivering a radiation beam with higher photon fluence at the patient's level.

5. A method according to claim 1 including the step of delivering a cleaner radiation beam at the patient's level.

6. A method according to claim 1 wherein the step of removing the flattening filter reduces lateral scatter.

7. A method according to claim 1 including the steps of:
   controlling planar fluence in the radiation source with a multi-leaf collimator (MLC); and
   inverse treatment planning to achieve uniformity within a target volume for the radiation beam without a flattening filter.

8. A method according to claim 1 wherein the linear accelerator is an IMRT capable radiation accelerator.

9. A method according to claim 1 wherein the MLC is used to achieve uniformity that conforms to convention 3D therapy treatments.

10. A method according to claim 1 including the step of varying fluence with a combination of MLC movements in and out of radiation field to produce beam modulation at the patient level.

11. A method according to claim 1 wherein the radiating delivers a 3D conformal gamma radiation dose to a treatment zone at the patient's level.

* * * * *